(12) United States Patent
Zmora

(10) Patent No.: US 6,560,308 B1
(45) Date of Patent: May 6, 2003

(54) METHOD AND SYSTEM FOR APPROXIMATING MISSING DATA IN CONE BEAM X-RAY CT RECONSTRUCTION

(75) Inventor: Ilan Zmora, Skokie, IL (US)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/983,819

(22) Filed: Oct. 26, 2001

(51) Int. Cl.[7] .................................................. A61B 6/03
(52) U.S. Cl. .............................. 378/4; 378/15; 378/901
(58) Field of Search ........................... 378/4, 8, 15, 901

(56) References Cited

U.S. PATENT DOCUMENTS 5,611,026 A * 3/1997 Eberhard et al. ........... 345/419
6,148,056 A * 11/2000 Lin et al. ....................... 378/4

OTHER PUBLICATIONS

Proceedings of the 1999 International Meeting on Fully Three-Dimensional Image Reconstruction in Radiology and Nuclear Medicine; Jun. 23–26, 1999; "An Iterative Approach to the Beam Hardening Correction in Cone Beam CT", pp. 87–91. By: Jiang Hsieh, et al.

* cited by examiner

Primary Examiner—David V. Bruce
(74) Attorney, Agent, or Firm—Oblon, Spivak, McClelland, Maier & Neustadt, P.C.

(57) ABSTRACT

A method and system for computed tomography. Data is collected along a circular trajectory of an x-ray source. Data missing from the circular data is approximated. This may be accomplished by generating data that would have been collected along a line trajectory of the x-ray source. The image is reconstructed using the circle data and the approximated data. The circle views may be reconstructed from the circle data using a conventional Feldkamp reconstruction while the line data that would have been collected may be reconstructed as a correction to the Feldkamp reconstruction. The correction may be made by image addition, by adding the pixel values of the images reconstructed from the circle data and the approximated line data.

39 Claims, 10 Drawing Sheets

METHOD AND SYSTEM FOR APPROXIMATING MISSING DATA IN CONE BEAM X-RAY CT RECONSTRUCTION

BACKGROUND OF THE INVENTION

1. Field of the Invention

The present invention relates to reconstruction in cone beam computed tomography (CT), and in particular to generating approximations to missing data in circular scan cone beam CT.

2. Discussion of the Background

In volume CT, or cone-beam CT, the x-ray scanner employs multi-row detector arrays and x-ray beam collimation that results in a cone-like shape of the x-ray beam, illuminating the whole area-detector. These two features coupled with ultra fast (such as 0.5 sec/rotation) rotation of the x-ray tube along a circular trajectory, provide the volume CT scanner with the capability to acquire large amounts of data in a very short time. The weakest point of volume CT is the lack of an adequate reconstruction method. The most common reconstruction method used in volume CT is the Feldkamp reconstruction (also known as cone-beam reconstruction). However when the scan geometry is such that large cone angles are involved, Feldkamp images suffer from serious artifacts. The reason for these artifacts is that the circle data is not a complete data set in the sense of 3-D tomography. The data set which is necessary to complement the circular data set into a complete data set is called the missing data.

Many attempts were made to improve the Feldkamp reconstruction based on ad hoc methods, but no robust solution was achieved. Although it was considered by it's inventors as an approximate cone beam reconstruction method, the Feldkamp reconstruction was shown later to be an exact method when the scan data is collected only along a circular trajectory. The problem is not the reconstruction algorithm but the fact that the data collected along a circular trajectory is incomplete. The missing data issue was first recognized by Grangeat who considered the circle trajectory scan from a fully 3D point of view.

Grangeat's theorem relates the processed cone beam x-ray transform (data collected by cone beam scanners) to the first derivative (with respect to the signed distance from the origin) of the 3D Radon transform. The 3D Radon transform is defined on planes, and therefore he considered the locus of all the vectors perpendicular to those planes for which the 3D Radon transform is required. He coined the name Shadow Zone given to the group of vectors for which the Radon transform on the corresponding planes can not be obtained by the circle scan. Using this graphical description Grangeat also proposed to obtain approximations of the data corresponding to the vectors in the Shadow Zone (missing data) by interpolation of the known data belonging to vectors on the border of the Shadow Zone. Grangeat proposed methods to approximate the missing data, but his methods of counting the planes, obtaining the approximations, and finally reconstructing all the data, are all very complicated and time consuming.

One way to solve the missing data issue is to use different scan geometry by performing the volume scan along a different trajectory. In the orthogonal line and circle scan, the data collected along the line complements the data collected along the circular trajectory into a complete data set. However, the addition of the linear motion of the couch results in the loss of the speed advantage of the volume scanner and subjects the patient to a much longer time in the scanner and to a higher radiation dose.

SUMMARY OF THE INVENTION

It is an object of the present invention to reconstruct images using approximated missing data.

It is a further object of the invention to approximate missing data and to reconstruct it, thereby improving the image quality of reconstructed images.

It is still further object of the invention to generate virtual line data that can complete circular data, improving reconstruction of images.

According to the invention, in approximating the missing data, data may be collected along a circular trajectory complemented by the data that could be collected along a line trajectory is a complete data set. The data that could be collected along the line trajectory is approximated, and used in the reconstruction of images.

These and other objects of the invention may be obtained by the method according to the invention where an image is reconstructed by scanning a stationary object along a circular trajectory to obtain projection data. Circle data is reconstructed from the projection data, and line data is approximated using the circle data. The image is reconstructed using the circle data and the approximated line data.

The circle data may be processed by weighting, integrating, differentiating and then dividing by co-inclination factor. The line data may be generated using the processed circle data.

The line data may be generated using edge planes. The edge planes pass through a line from a particular focal spot position to a detector cell and touch the scan circle at one point. Data related to the edge planes can be obtained from data collected along the scan circle.

Approximating the line data may comprise generating line data that will complete a circular data set corresponding to the circle data.

The circle data may be reconstructed using a Feldkamp reconstruction technique and the image may be reconstructed using a method based upon a Kudo and Saito algorithm.

The method according to the invention may also comprise scanning a stationary object along a circular trajectory to obtain image data, reconstructing circle data from the image data, approximating line data using the circle data and correcting the circle data using approximated line data.

The present invention is also directed to a computed tomography apparatus having an x-ray source for exposing an object to a cone beam of x-rays, and an x-ray detector arranged to receive the beam of x-rays. In one embodiment, a first reconstruction processor is connected to the data acquisition device to reconstruct a circle view from the projection data, a missing data calculator is connected to the data acquisition device to calculate data missing from the circle view, a line data processor is connected to the missing data calculator, a second reconstruction processor is connected to the line data processor, and an image addition processor is connected to the first and second reconstruction processors.

DESCRIPTION OF THE PREFERRED EMBODIMENTS

Figure 1:
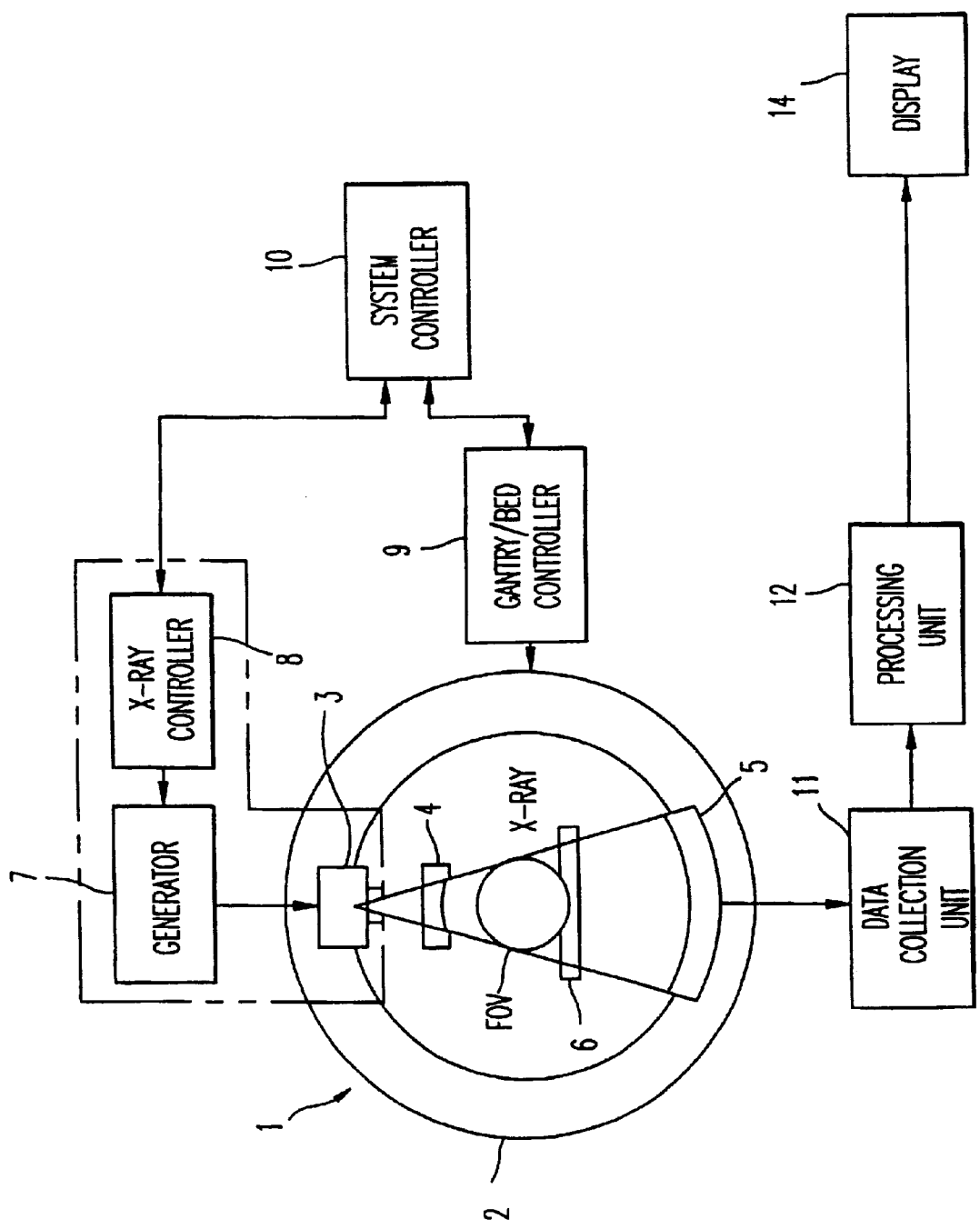
FIG. 1 is a diagram of the system according to the invention.
Figure 2:
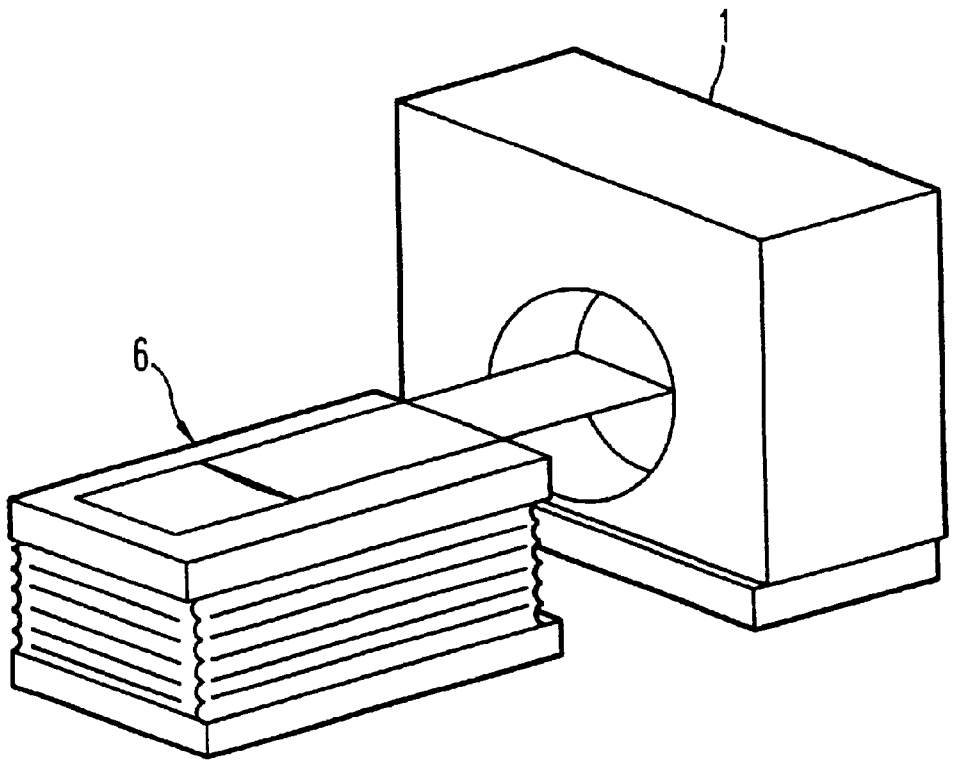
FIG. 2 is a perspective view of the system according to the invention.

The present invention is directed to a system and method for approximating data missing when a circular scan is performed. Referring now to the drawings, wherein like reference numerals designate identical or corresponding parts throughout the several views, and more particularly to FIG. 1 which is a diagram of the system according to the invention. A gantry 1 accommodates an x-ray source 3 that generates a beam of x-rays. The beam is preferably a cone-beam. An x-ray detector 5 receives the x-rays emitted from source 3 after penetrating the object contained in a circle indicated as field of view (FOV). X-ray source 3 and detector 5 are installed on a rotating ring 2. The system 'may also include an x-ray filter 4 which may be coupled to rotating ring 2. The object is typically laid on a sliding sheet of a bed 6. FIG. 2 is a perspective view of the system according to the invention, Bed 6 moves into the cylindrical cavity of system 1.

X-ray controller 8 supplies a trigger signal to high voltage generator 7. High voltage generator 7 applies a high voltage to x-ray source 3 based upon the received trigger signal. X-rays are emitted by x-ray source 3 and gantry/bed controller 9 controls the revolution of rotating ring 2 of gantry 1 and the sliding of the sliding sheet of bed 6 to scan the object. System controller 10 constitutes a control center of the entire system and controls the x-ray controller 8 and gantry/bed controller 9. X-ray source 3 executes scanning, preferably along a rotational path on a stationary object. With a large number of detector rows (described below), one rotation is usually sufficient to image the area of interest in the object. However, the invention is not limited to rotational scanning and other scanning techniques may be used such as helical.

The output signal of the detector 5 is amplified by data collection unit 11 and converted into a digital signal to produce projection data. Data collection unit 11 also outputs image data 15 to processing unit 12. Processing unit 12 processes the data using reconstruction techniques to produce output images. The output image may be output to output device 14. Output device 14 may consist of a video display terminal, a laser printer, another output device, or a combination of these.

Figure 3:
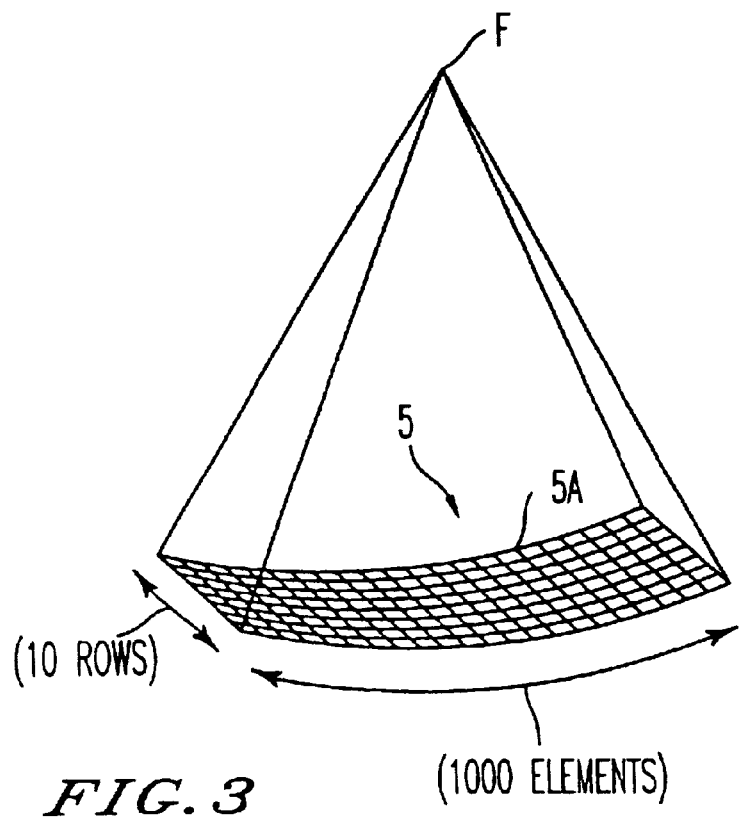
FIG. 3 is a diagram of a multi-row detector.

A more detailed view of detector 5 is shown in FIG. 3. Detector 5 contains a plurality of rows 20 of detector elements 21. Eight rows are shown in FIG. 3, but the number of rows may be as many as 512. With a large number a detector rows, compared to the small number typically used, one circular rotation around the object is usually sufficient. Also, certain considerations may be taken into account. For example, a larger number of detector rows produce a much larger amount of data, which have to be transferred, processed and stored at the same time, or even at shorter times. The processors and communication devices should be fast, and storage devices should have large capacities. The present invention is especially suited for reconstructing images using detectors having a large number of rows of detectors.

The detector may be flat or curved. The following will refer to a system having a flat detector. A system with a curved detector may contain special software or hardware to transform the data set collected by the curved detector into a data set equivalent to what would be collected by a flat detector. This will be done typically by the collector unit 11, or by the processing unit 12.

Figure 4:
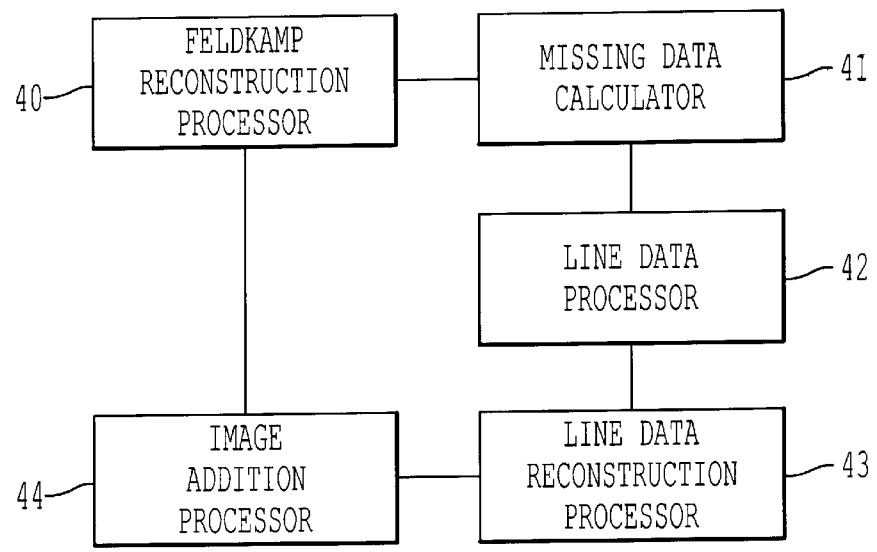
FIG. 4 is a block diagram of the processing unit of FIG. 1.

Processing unit 12 may consist of a programmed general purpose computer or may be a programmed microprocessor more specifically designed for image processing. In the former case, the software run on the general purpose computer handles the image reconstruction, data and memory management, and other data processing tasks. FIG. 4 is a block diagram of one example of the processing unit according to the invention, the operation of which is described in more detail below. A Feldkamp reconstruction processor 40 performs Feldkamp reconstruction, while, possibly in a separate pipe line, missing data calculator 41 calculates the missing data (virtual line data) and arranges it in line data format. Line data processor 42 processes the virtual line data and prepares it for reconstruction. The line data reconstruction processor 43 generates the line data (correction) images. Finally the image addition processor 44 combines the Feldkamp images with their corresponding corrections. The images and the corrections are added by simple addition of pixel values.

Figure 5:
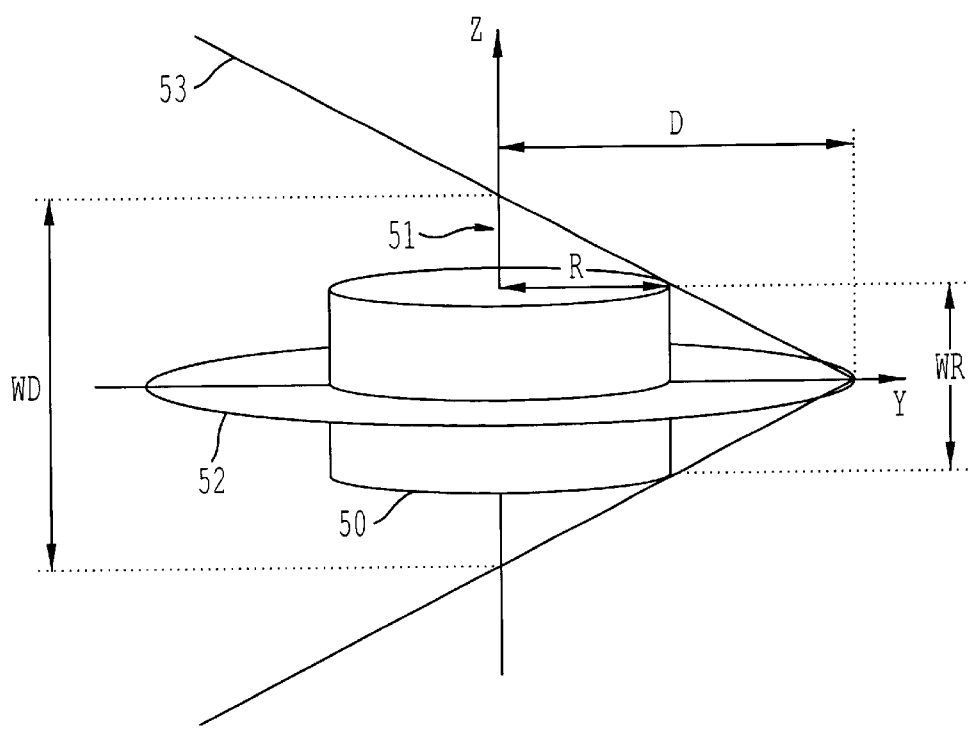
FIG. 5 is a diagram illustrating the system geometry and scan coordinate system used in the invention.

The parameters in scanning and reconstructing images will now be described. Conventionally, orthogonal line and circle scans are performed in 2 steps. During the first step the x-ray tube and the area detector move in a circular trajectory in one plane, and during the second part the x-ray tube and the area detector move along a line which is perpendicular to the plane containing the circular trajectory. The line trajectory is typically accomplished by translating the bed while holding the x-ray source stationary. FIG. 5 illustrates the system geometry and scan coordinate system. A fixed coordinate system is chosen to describe both parts of the scan. FIG. 5 (and FIGS. 6A and 6B) are not to scale. The z-dimension is much more emphasized (enlarged) than the x- and y-dimensions. The X-Y plane of this system coincides with the plane containing the circular trajectory, and the origin of the system coincides with the center of the circular motion.

The mid-plane is the X-Y plane (corresponding to Z=0) of the scan coordinate system. The axis of rotation 51 is perpendicular to the mid-plane, intersecting it at the origin. The scan circle 52 is the circular trajectory of the focal spot in the mid-plane, which is centered at the origin. D is the radius of the scan circle 52 and FOV is the diameter of the circular area to be reconstructed on the midplane. In FIG. 5, R=FOV/2. The volume to be reconstructed, or reconstruction ROI is given as 50. This is a cylinder of radius R, and height $W_R = W_D(D-R)/D$, centered at the origin, where $W_D$ is the height of the detector (number of rows times the width of one row). The scan line is the (virtual) linear trajectory of the focal spot. The scan line is perpendicular to the midplane, and it intersects the midplane at the point (0,−D,0), at a distance D from the origin. The coordinates of a general point on the scan line is (0,−D,F), where F is the distance from the mid-plane. Here, $F_{MAX}$ is the length of the scan line in each direction (total length is $2F_{MAX}$) necessary to cover the reconstruction ROI, and is given by $F_{MAX}=W_D$. The cone beam of x-rays is given as 53.

Another parameter is the detector (or moving) coordinate system ($X_D$, $Z_D$). This is a coordinate system moving with the area detector both along the circular trajectory, and along the linear trajectory. The origin of this coordinate system is at the center of the detector. A general point on the detector is denoted by coordinates as ($X_D$, $Z_D$). The detector cells form a grid of points at ($X_{Di}$, $Z_{Dj}$) where $$Z_{Dj} = (j-C_S)\Delta s,$$

where $C_{S=N_S}/2+0.5$ $$X_{Di} = (i-C_C)\Delta_C,$$

where $C_{C=N_C}/2+0.5$
$\Delta_S$ and $\Delta_C$ are the detector spacing in the horizontal and vertical directions respectively, and $N_S$ and $N_C$ are the number of detector cells along one row and one column respectively.

Figure 6A:
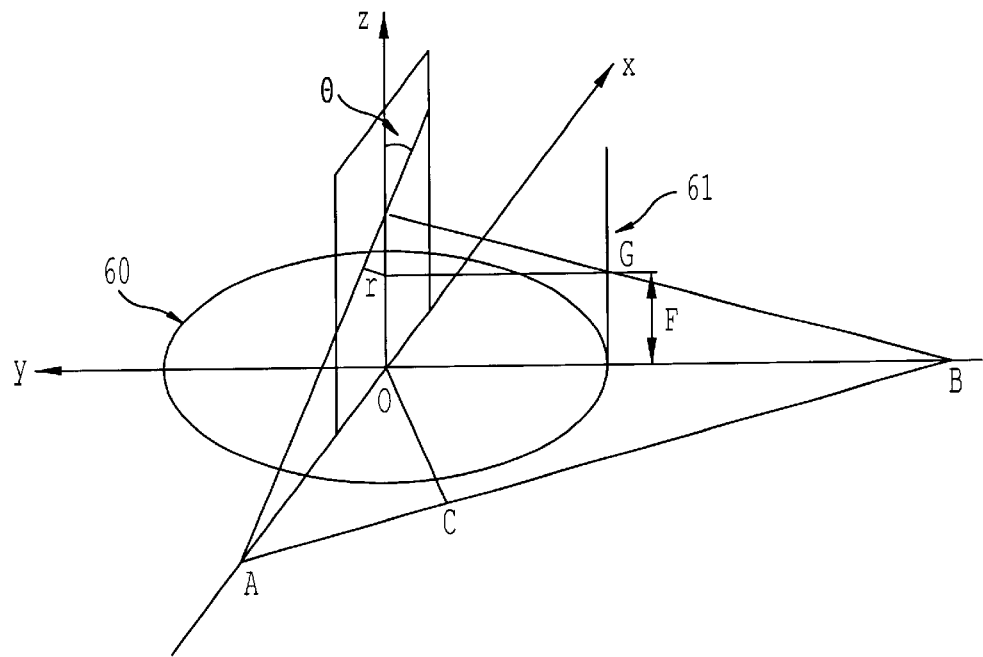
FIG. 6A shows the parameters of the planes in the detector coordinate system.

FIG. 6A shows the parameters of the planes in the detector coordinate system. The equation of a line in the detector coordinate system can be written as:

$$r = X_D \cos\theta + Z_D \sin\theta$$

where ($X_D$, $Z_D$) is any point on the line. The two parameters, r and θ, are used to characterize this line. A line (r, θ) on the detector board and a point F on the scan line define a plane (F,r,θ). FIG. 6A illustrates the circular trajectory 60 and the linear trajectory 61. Points A, B, C are the intersections of the plane with the x, y and z axes, respectively, and point G is the intersection of the plane with the linear trajectory.

Figure 7:
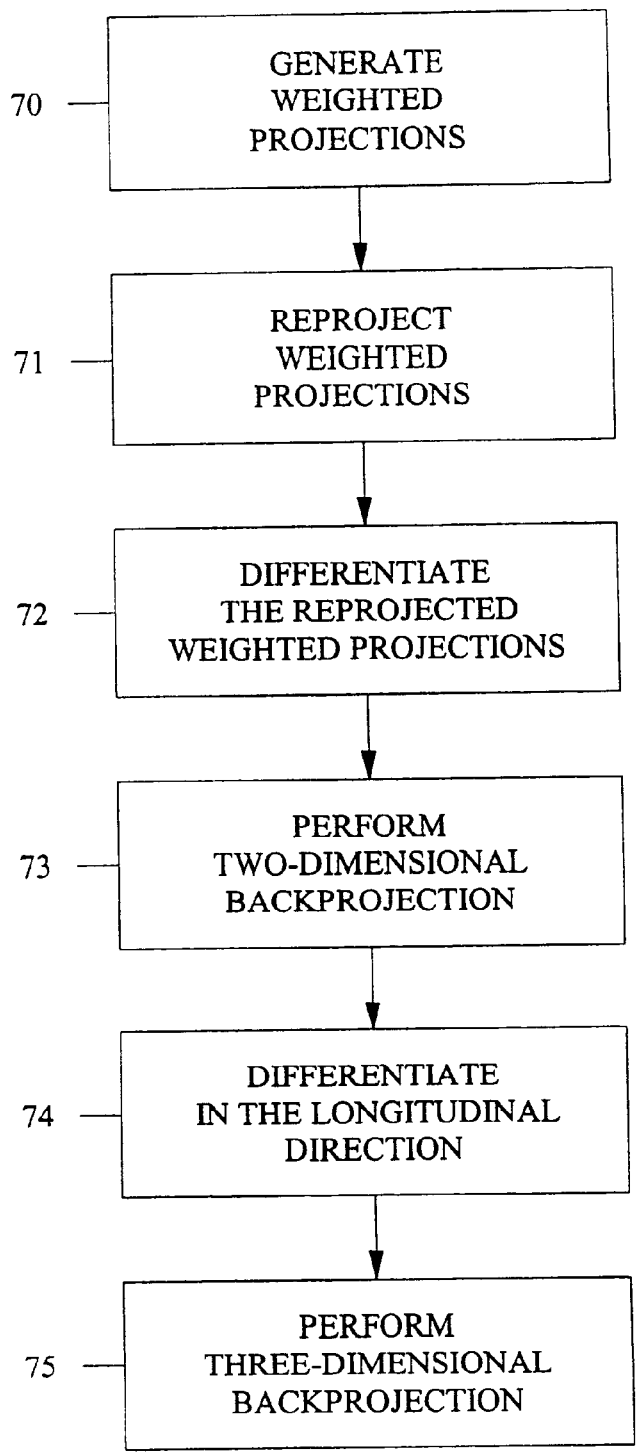
FIG. 7 is a diagram of processing of line views.

Reconstruction of the line and circle data may be performed using the Kudo and Saito method. The reconstruction according to Kudo and Saito can be divided into two parts. First, the circle views $P_\beta(X_D, Z_D)$ are processed, which is done according to the conventional Feldkamp reconstruction. Secondly, the line views $P_F(X_D, Z_D)$ are processed, which can be described in terms of the following six steps illustrated in FIG. 7. First, weighted projections are generated (step 70), and can be determined according to the following equation.

$$P_F^W(X_D, Z_D) = \frac{D}{\sqrt{D^2 + X_D^2 + Z_D^2}} P_F(X_D, Z_D)$$

In step 71, Re-projection (integration) of the weighted projections takes place, and can be determined according to the following equation.

$$G_F(r, \theta) = \int_{-\infty}^{+\infty}\int_{-\infty}^{+\infty} dX_D\, dZ_D P_F^W(X_D, Z_D)\delta(r - X_D\cos\theta - Z_D\sin\theta)$$

The reprojected weighted projections are then differentiated in the radial direction in step 72, and can be done using the following equation.

$$G_F^{(1)}(r, \theta) = \frac{\partial}{\partial r} G_F(r, \theta)$$

Figure 8:
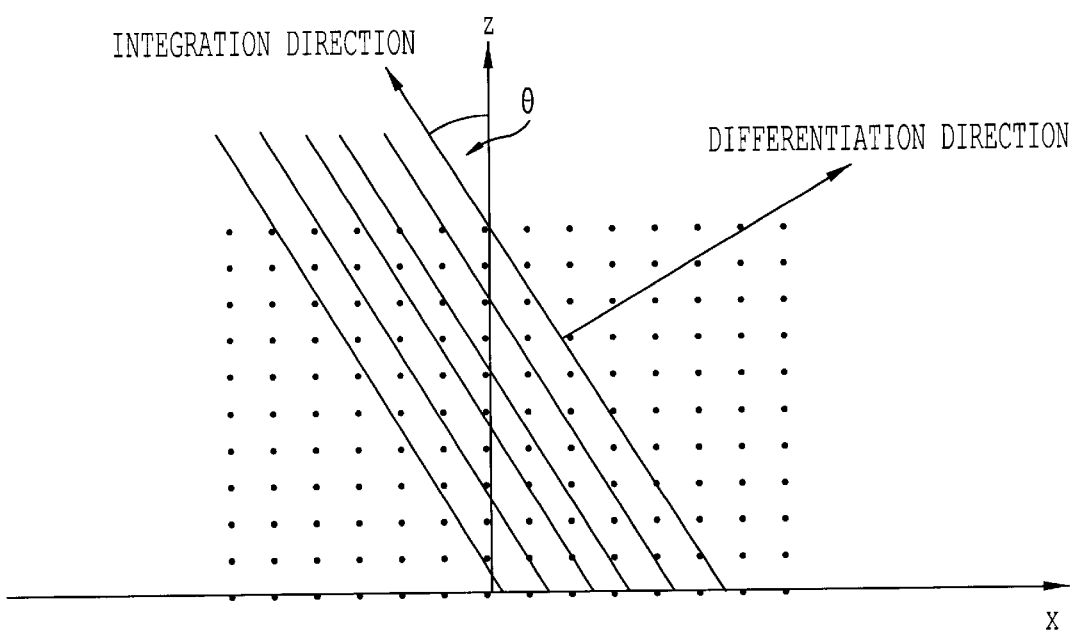
FIG. 8 is a diagram illustrating integration and differentiation directions for a line data set belonging to one focal spot position.

FIG. 8 illustrates the integration and differentiation directions for a data set belonging to one focal spot position.

In step 73 two-dimensional back-projection is performed, and may be done in the following manner.

$$P_F^B(X_D, Z_D) = \int_{\theta_1(F, X_D, Z_D)}^{\theta_2(F, X_D, Z_D)} d\theta G_F^{(1)}(X_D\cos\theta + Z_D\sin\theta, \theta)$$

The integration limits in the 2D back-projection are defined so as to prevent over-counting of contributions that were already counted in the Feldkamp reconstruction:

$$tg\theta_1 = \frac{-X_D F + \sqrt{F^2(X_D^2 + D^2) + 2D^2 F Z_D}}{F^2 + 2F Z_D}$$

$$tg\theta_2 = \frac{-X_D F - \sqrt{F^2(X_D^2 + D^2) + 2D^2 F Z_D}}{F^2 + 2F Z_D}$$

The result is differentiated in the longitudinal direction (step 74)

$$P_F^{(1)}(X_D, Z_D) = \frac{\partial}{\partial Z_D} P_F^B(X_D, Z_D)$$

Finally (step 75) the contribution of the line views to the image is obtained by three dimensional back projection of the quantity $$P_F^{(1)}(X_D, Z_D)$$

to yield the line image.

In a scan, the data collected along the circular trajectory, after undergoing corrections and some initial processing, is arranged in matrices $P_\beta(X_{Di}, Z_{Dj})$. Each matrix of data, or circle view corresponds to one angular position β along the circle, and the entries of the matrix correspond to the grid of detector cells. As discussed above, there is data missing from the data necessary to reconstruct the image. According to the present invention, the missing data are approximated and arranged in virtual line data format. These are matrices $P_F(X_{Di}, Z_{Dj})$ where each matrix of data, or line view, corresponds to one position F along the scan line, and the entries of the matrix correspond to the grid of detector cells. The line data processing is related to the Radon Transform on planes that intersect the object.

Figure 9:
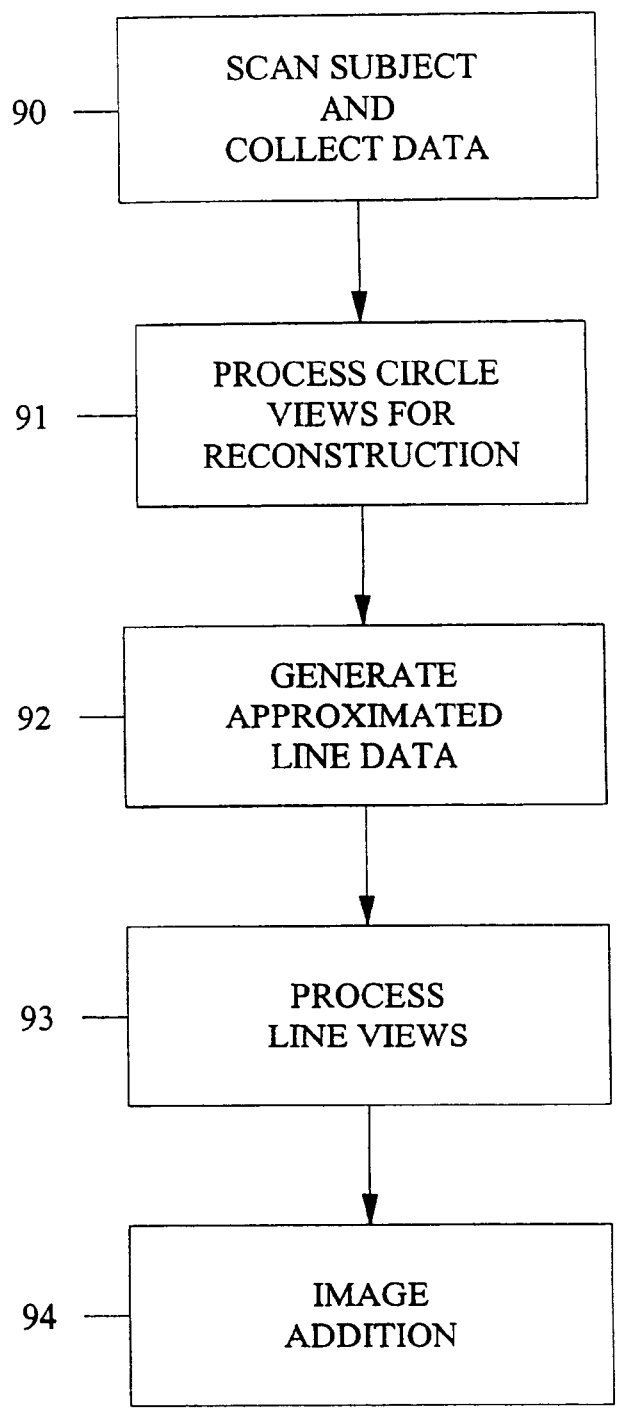
FIG. 9 is a diagram of a first embodiment of the method according to the invention.

The method according to the invention will be generally described in connection with FIG. 9. In step 90 an object is scanned and volume data is collected. In the system of FIG. 1, the x-ray source is rotated on the gantry and the object is kept stationary, resulting in a circular scan, which is the scan of choice of this system. The data is collected using the data collection unit 11. As discussed above, the data may be arranged in matrices $P_\beta(X_{Di}, Z_{Dj})$ where each matrix, or circle view, corresponds to one angular position β along the circle.

The circle views are reconstructed using the Feldkamp reconstruction, by processing unit 12 (step 91). Sectional images result. Next, in step 92, data missing from the circular views is approximated, again by processing unit 12. This step does not need to occur after step 91, but can proceed once the data is collected. The line views are processed (described below) in step 93. The image is reconstructed with the circle views and approximated line views by image addition (pixel value, addition) in step 94. In more detail, as shown in FIG. 4, the circle views are reconstructed by processor 40, and the missing data is calculated by calculator 41. Processor 42 processes the line image and processor 43 reconstructs the line data. The two reconstructed views are added by pixel addition by processor 44.

Figure 10:
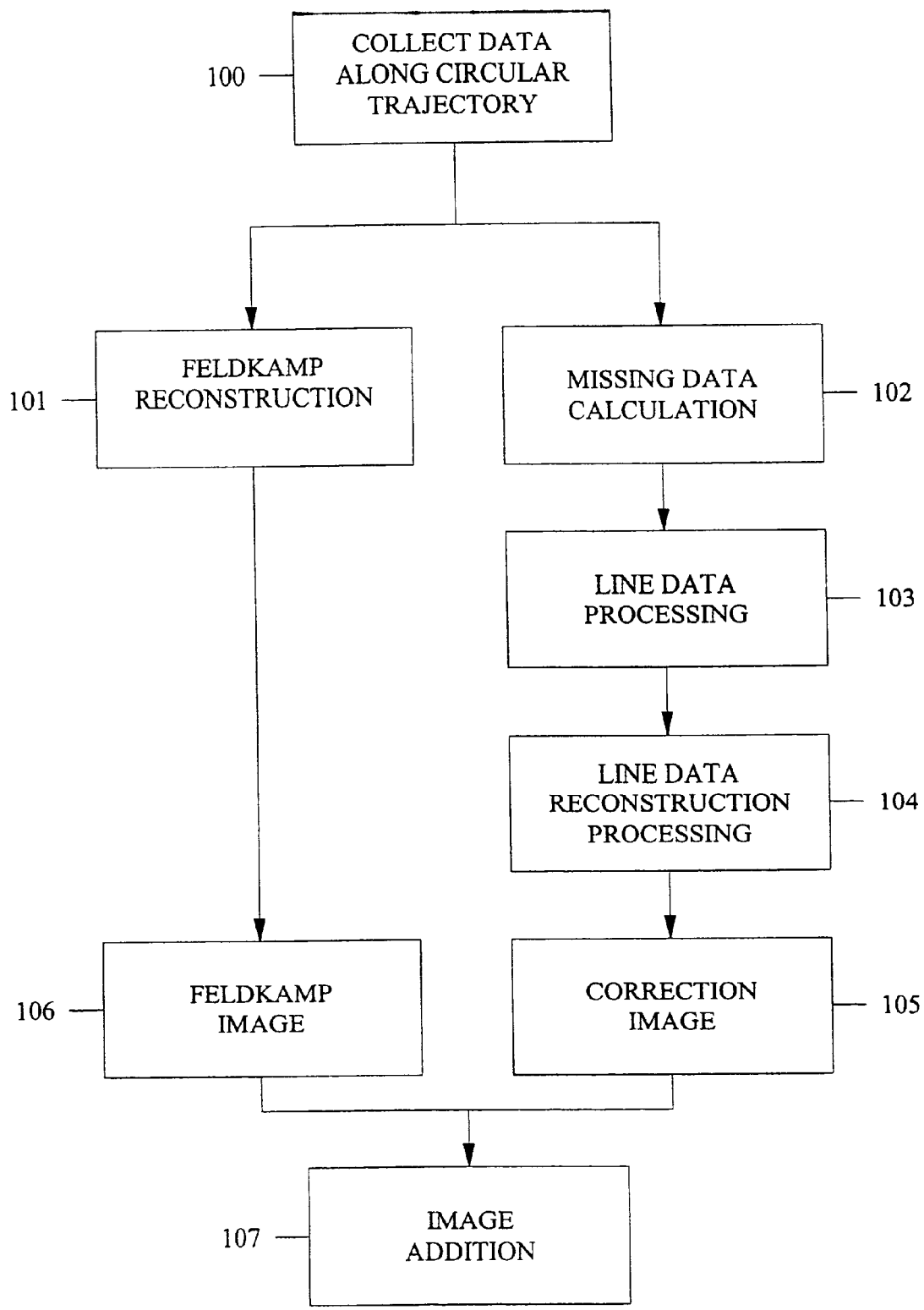
FIG. 10 is a more detailed diagram of the method according to the invention.

FIG. 10 illustrates the method according to the invention where the processing of the circle views and the approximation of the line is shown to be conducted in parallel. In other words, the approximation of the line data does not have to wait for the circle view processing, and vice versa. In step 100 data is collected on a circular trajectory. This data is used in step 101 to process the circle views by Feldkamp reconstruction to yield a Feldkamp image 106. The circle data, in a parallel path, is used in the missing data calculation step 102, line data processing step 103 and line data reconstruction step 104 to yield a line or correction image 105. The images 105 and 106 are added, by pixel addition, in step 107.

The method according to the invention will now be described in more detail. The orthogonal line and circle geometry (FIG. 6A) is used to count the missing data (parameterization), by forming a one-to-one correspondence between the missing data and the data that would have been acquired along the line trajectory. According to this correspondence, the missing data, in principle, is arranged in the same matrices $P_F(X_{Di}, Z_{Dj})$, which are given the same interpretation as the data that would have been collected if a line scan had been performed. The (i,j) entry of the matrix $P_F(X_{Di}, Z_{Dj})$ is be arranged in the same matrices $P_F(X_{Di}, Z_{Dj})$, which are given the same interpretation as the data that would have been collected. This means that the (i,j) entry of the matrix $P_F(X_{Di}, Z_{Dj})$ constitutes an approximation of the projection value of the particular ray that emanated from the x-ray focal spot position on the scan line at a distance F from the mid-plane and passed through the detector cell $(X_{Di}, Z_{Dj})$. However the actual calculation of approximated values may be performed at a later stage, after the data that would have been collected undergoes some initial processing according to the Kudo and Saito algorithm.

The quantities derived in the processing, which are still arranged in matrices, can be used in the approximation. These derived quantities can be interpreted in terms of the derivative of the Radon Transform values belonging to planes passing through the scan object. Considering the reconstruction according to Kudo and Saito (described above), in the generation of the real values of the derived quantities, a particular entry of the matrix $$P_F^B(X_{Di}, Z_{Dj})$$

obtains contributions from a certain group of planes. These planes can be characterized as follows: (a) they all contain the same point (or focal spot position) on the scan line (at a distance F from the mid-plane) and the center of the detector cell denoted by the coordinates $(X_{Di}, Z_{Dj})$, in other words they all pass through the line from the particular focal spot position to the detector cell, and (b) they do not cross the scan circle. According to the invention, the value of the Radon Transform on each of the planes in the group is derived, by interpolation, from the 'edge planes', i.e. the 2 planes belonging to the group and just touching the scan circle. It follows that the derived quantities can also be derived in the same way.

Figure 6B:
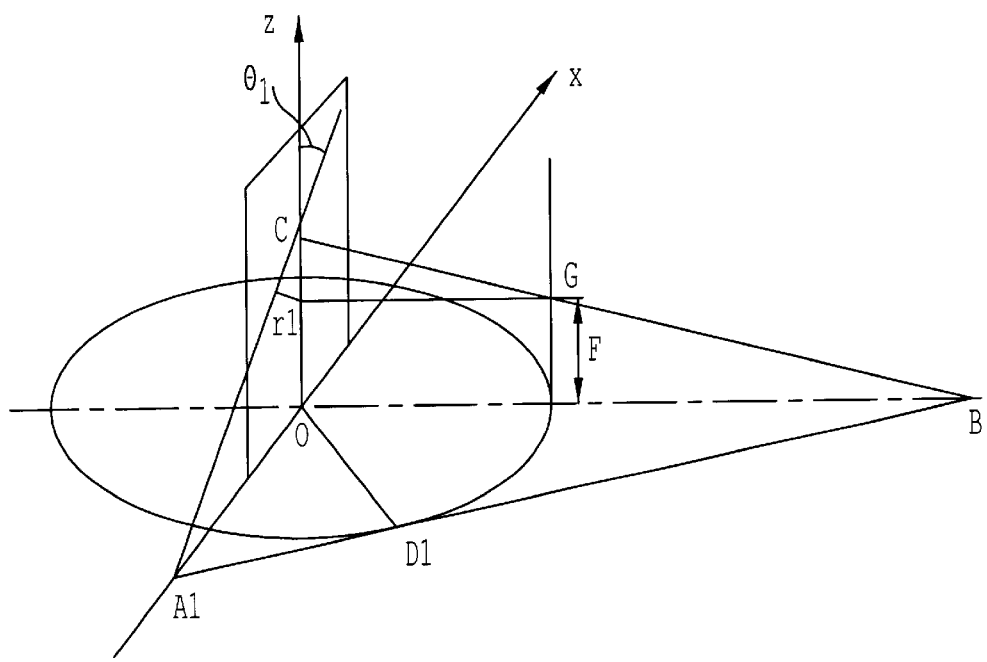
FIG. 6B shows the parameters of an edge plane in the detector coordinate system.

FIG. 6B shows one 'edge' plane characterized by coordinates r and θ. It intersects the axes X, Y, Z at the points A, B, C. The line OD is the perpendicular from the origin to the line AB. The plane belongs to the set of planes that contain the line GC. Considering all of the planes that contain this line, i.e., a plane is rotated along this line, only two planes touch the scan circle. These planes are called edge planes. The plane (r1, θ1) in FIG. 6B is an edge plane which was obtained from the plane (r, θ), by rotation around line GC until it just touches the scan circle (point D1 is on the circle). Since the edge planes touch the scan circle, the data related to them can be obtained from the data collected along the scan circle. Calculation of the contributions from all of the planes are obtained from the two edge planes.

Figure 6C:
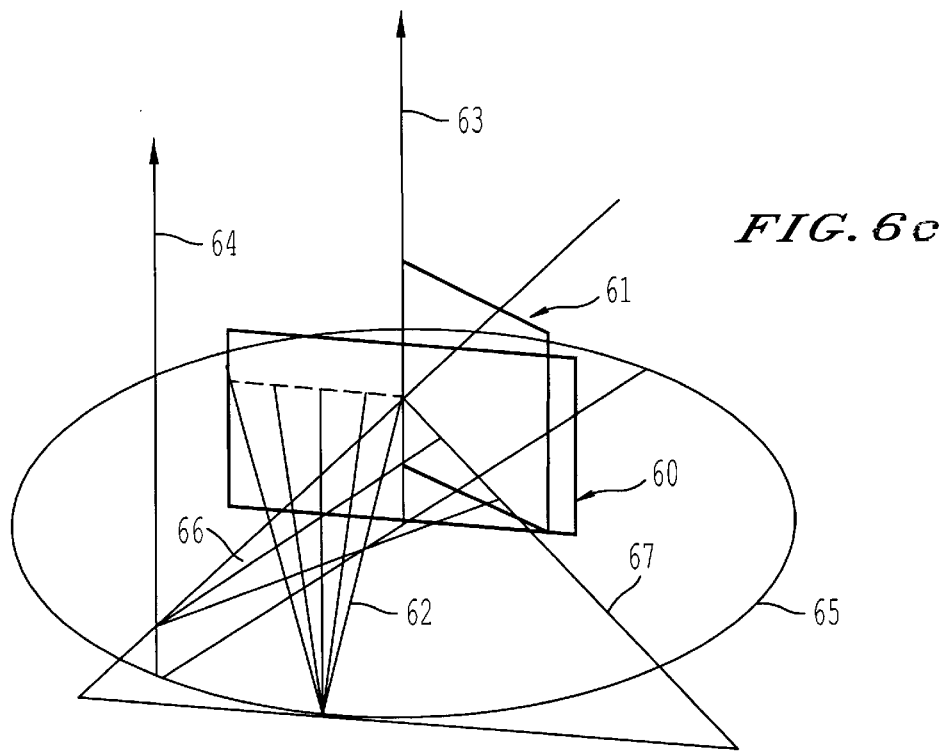
FIG. 6C shows edge plane parameters.

FIG. 6C shows an edge plane in connection with the detector in both the line and circle scans. Shown are the detector position 60 in an example circle scan 65, and position 61 in a linear scan trajectory 64, with the z-axis is 63 given for reference. The x-ray beam in the circle scan is 62, the in the linear scan is 66. The edge plane is indicated as 67.

Figure 11:
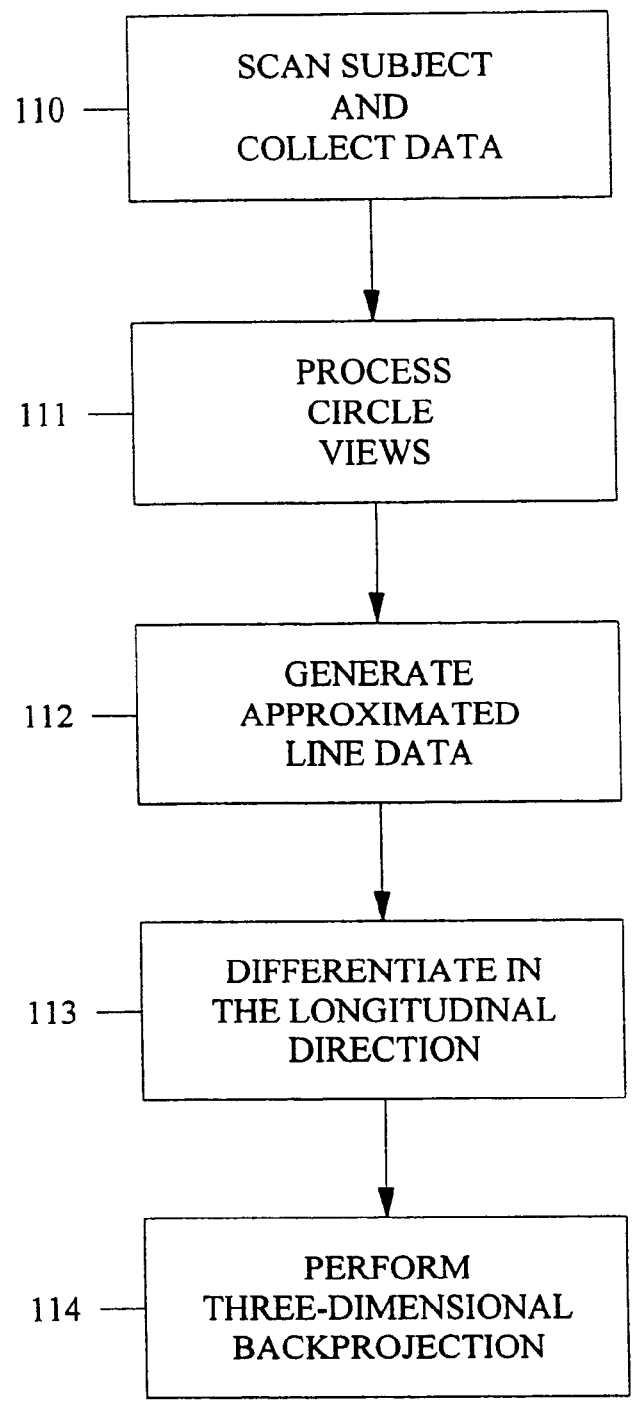
FIG. 11 is a diagram of the method according to the invention.
Figure 12:
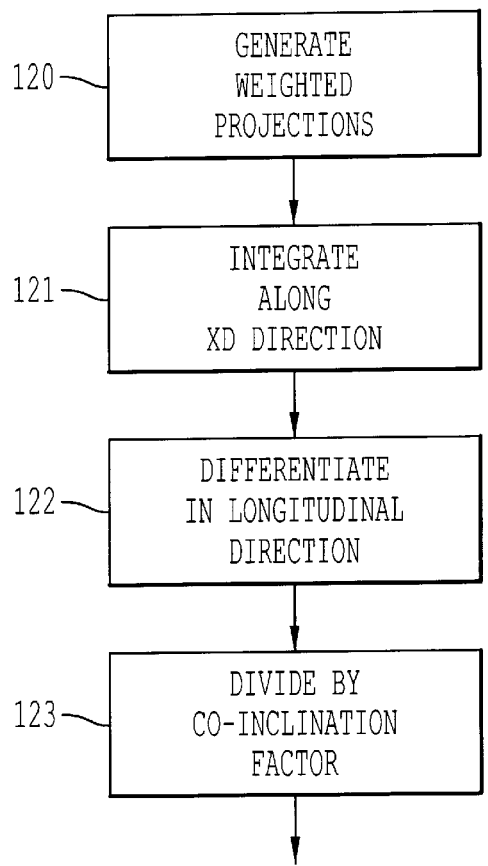
FIG. 12 is a more detailed diagram of the circle view processing step of the method of FIG. 11.

The operations required for the calculation using the edge planes within the framework of the Kudo and Saito method is now described. Referring to FIG. 11, after scanning and collecting data (step 110), the circle data is processed view by view (step 111). This may be done separate from processing for the Feldkamp reconstruction, as discussed above. FIG. 12 shows this step in more detail. In step 120 weighted projections are generated using, $$P_\beta^W(X_D, Z_D) = \frac{D}{\sqrt{D^2 + X_D^2 + Z_D^2}} P_\beta(X_D, Z_D)$$

These values are integrated along the $X_D$ direction (step 121), using, $$P_\beta^{(1)}(Z_D) = \int_{-\infty}^{+\infty} dX_D P_\beta^W(X_D, Z_D)$$

then differentiated in the longitudinal direction (step 122) using, $$P_\beta^{(2)}(Z_D) = \frac{\partial}{\partial Z_D} P_\beta^{(1)}(Z_D)$$

and divided by the co-inclination factor (step 123) as $$P_\beta^{(3)}(Z_D) = \frac{P_\beta^{(2)}(Z_D)}{\sin^2 \gamma}$$

where γ is the inclination angle of the plane that contains the focal spot position corresponding to view β and intersects the area detector along the line of detector cells all having coordinate $Z_D$.

Figure 13:
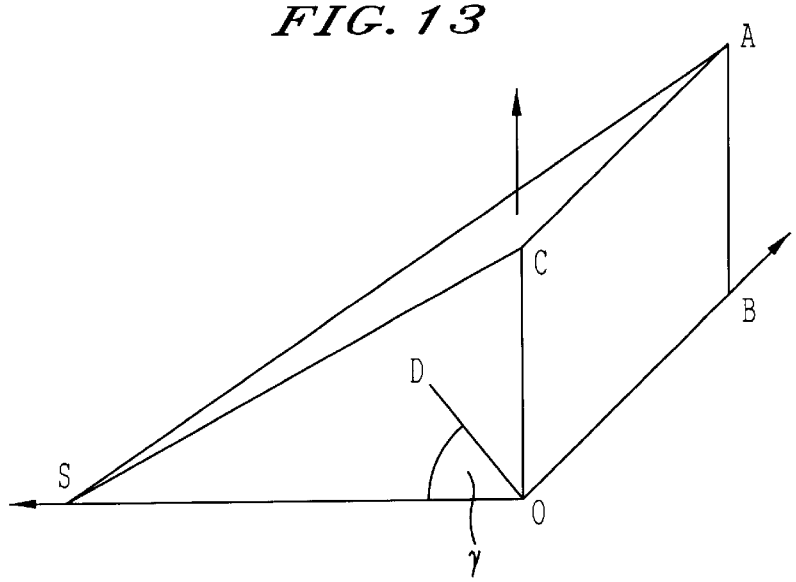
FIG. 13 is a diagram illustrating the inclination angle.

The inclination angle is defined with respect to a plane SAC intersecting both the focal spot trajectory (at the focal position S) and the area detector ACOB (see FIG. 13). It is the angle between the line SO from the origin O of the detector system to the focal spot position S, and the perpendicular OD from the origin to the plane SAC.

The approximated line data is then generated (step 112). This operation replaces the data obtained in the first four steps (of the Kudo and Saito method shown in FIG. 7) used in the processing of the real line scan data described above with data obtained from the additional processing of the circle data as follows:

$$\frac{\theta_2-\theta}{\theta_2-\theta_1}\left[P^{(3)}_{\beta_1}\left(F+Z_D+\frac{X_D}{tg\theta_1}\right)\sin^2 Y_1\right]+\frac{\theta-\theta_1}{\theta_2-\theta_1}\left[P^{(3)}_{\beta_2}\left(F+Z_D+\frac{X_D}{tg\theta_2}\right)\sin^2 Y_2\right]$$

where $\theta_1$ and $\theta_2$ are defined by the equations for $tg\theta_1$, and $tg\theta_2$ (as above, in the Kudo and Saito processing), $\gamma_1$ is the co-inclination angle of the first edge plane and $\gamma_2$ is the co-inclination angle of the second edge plane. Here, $P_{\beta_1}^{(3)}$ and $P_{\beta_2}^{(3)}$ are the data for the two edge planes.

The circle view angles are defined by $$tg\beta_1 = -\frac{R}{Z_D tg\theta_1 + X_D}$$

$$tg\beta_2 = -\frac{R}{Z_D tg\theta_2 + X_D}$$

In the equation above the only quantities depending on $\theta$ are those before the square brackets and this leads to $$\tilde{P}^B_F(X_D, Z_D) =$$

$$\frac{1}{2}(\theta_2-\theta_1)\left[P^{(3)}_{\beta_1}\left(F+Z_D+\frac{X_D}{tg\theta_1}\right)\sin^2 Y_1 + P^{(3)}_{\beta_2}\left(F+Z_D+\frac{X_D}{tg\theta_2}\right)\sin^2 Y_2\right]$$

The virtual line data $P_F^B$ is thus determined from the acquired data for the edge planes. The data is then differentiated in the longitudinal direction and 3D back-projection is performed (steps 113 and 114), using the approximated data instead of the real data. Differentiation in the longitudinal direction is given by:

$$P^{(1)}_F(X_D, Z_D) = \frac{\partial}{\partial Z_D}\tilde{P}^B_F(X_D, Z_D)$$

and three-dimensional back-projection of the processed approximated line data to obtain the image used for correction. As shown in FIG. 9, the line data is used in image addition with the Feldkamp image to produce the desired image.

Obviously, numerous modifications and variations of the present invention are possible in light of the above teachings. For example, the method according to the invention may be performed in software. A computer program product may contain code devices to carry out the steps of the method on a general purpose computer. The invention may also be embodied as a software method on a recording medium such as an optical disk or magnetic disk. It is therefore to be understood that within the scope of the appended claims, the invention may be practiced otherwise than as specifically described herein.

What is claimed and desired to be protected by Letters Patents is:

1. A method of reconstructing an image, comprising:
   scanning an object along a circular trajectory to obtain projection data;
   reconstructing circle data from said projection data;
   generating approximated line data using said projection data; and
   reconstructing said image using said circle data and said approximated line data.

2. A method as recited in claim 1, comprising:
   weighting said projection data to give first data;
   integrating said first data to give second data;
   differentiating said second data to give third data; and
   dividing said third data by a co-inclination factor to give fourth data.

3. A method as recited in claim 2, comprising:
   reconstructing said image using said circle data and said fourth data.

4. A method as recited in claim 2, comprising:
   generating said line data using said fourth data.

5. A method as recited in claim 2, comprising:
   generating said line data using data at edge planes in said projection data.

6. A method as recited in claim 1, wherein generating said approximated line data comprises:
   generating line data that will complete a circular data set corresponding to said circle data.

7. A method as recited in claim 1, wherein:
   said scanning step produces an incomplete circular data set; and
   generating said approximated line data comprises generating data to complete said circular data set.

8. A method as recited in claim 1, comprising:
   reconstructing said circle data using a Feldkamp reconstruction technique.

9. A method as recited in claim 1, wherein said approximated line data is given as $P_F(X_D, Z_D)$, and said method comprises:
   generating weighted projections from data $P_\beta(X_D, Z_D)$ using:

$$P^W_\beta(X_D, Z_D) = \frac{D}{\sqrt{D^2+X_D^2+Z_D^2}}P_\beta(X_D, Z_D)$$

where D is a radius of a scan circle, integrating in an $X_D$ direction using:

$$P^{(1)}_\beta(Z_D) = \int_{-\infty}^{+\infty} dX_D P^W_\beta(X_D, Z_D)$$

differentiating in a longitudinal direction using:

$$P^{(2)}_\beta(Z_D) = \frac{\partial}{\partial Z_D}P^{(1)}_\beta(Z_D)$$

and dividing by a co-inclination factor:

$$P^{(3)}_\beta(Z_D) = \frac{P^{(2)}_\beta(Z_D)}{\sin^2 Y}$$

where $\gamma$ is the inclination angle of a plane that contains a focal spot position corresponding to view $\beta$.

10. A method as recited in claim 9, comprising:
    generating approximated line data using:

$$\frac{\theta_2-\theta}{\theta_2-\theta_1}\left[P^{(3)}_{\beta_1}\left(F+Z_D+\frac{X_D}{tg\theta_1}\right)\sin^2 Y_1\right]+\frac{\theta-\theta_1}{\theta_2-\theta_1}\left[P^{(3)}_{\beta_2}\left(F+Z_D+\frac{X_D}{tg\theta_2}\right)\sin^2 Y_2\right]$$

where $\theta_1$ and $\theta_2$ are defined as $$tg\theta_1 = \frac{-X_D F + \sqrt{F^2(X_D^2 + D^2) + 2D^2 F Z_D}}{F^2 + 2FZ_D}$$

$$tg\theta_2 = \frac{-X_D F - \sqrt{F^2(X_D^2 + D^2) + 2D^2 F Z_D}}{F^2 + 2FZ_D}$$

$\gamma_1$ is a co-inclination angle of a first edge plane, $\gamma_2$ is a co-inclination angle of a second edge plane, and $P_{\beta_1}^{(3)}$ and $P_{\beta_2}^{(3)}$ are data for two edge planes.

11. A method as recited in claim 10, comprising:

defining circle view angles by:

$$tg\beta_1 = -\frac{R}{Z_D tg\theta_1 + X_D}$$

$$tg\beta_2 = -\frac{R}{Z_D tg\theta_2 + X_D}$$

and generating line data as:

$$\tilde{P}_F^B(X_D, Z_D) =$$
$$\frac{1}{2}(\theta_2 - \theta_1)\left[P_{\beta_1}^{(3)}\left(F + Z_D + \frac{X_D}{tg\theta_1}\right)\sin^2\gamma_1 + P_{\beta_2}^{(3)}\left(F + Z_D + \frac{X_D}{tg\theta_2}\right)\sin^2\gamma_2\right].$$

12. A method as recited in claim 11, comprising:

differentiating said line data:

$$P_F^{(1)}(X_D, Z_D) = \frac{\partial}{\partial Z_D}\tilde{P}_F^B(X_D, Z_D)$$

and performing three-dimensional back-projection after said differentiating.

13. A method as recited in claim 1, comprising:

scanning a stationary object along said circular trajectory to obtain said projection data.

14. A method as recited in claim 1, comprising:

generating said approximated line data using projection data from edge planes.

15. A method as recited in claim 1, comprising:

generating said approximated line data using two planes in said projection data each contacting a scan circle only at a point.

16. A method of reconstructing an image, comprising:

scanning an object along a circular trajectory to obtain image data;

reconstructing circle data from said image data;

approximating line data using said image data to create approximated line data; and correcting said circle data using said approximated line data.

17. A method as recited in claim 16, comprising:

scanning a stationary object along said circular trajectory to obtain said image data.

18. A method as recited in claim 16, wherein reconstructing said circle data comprises:

generating weighted projections of said image data;

integrating said weighted projections; and differentiating said weighted projections in a radial direction.

19. A method as recited in claim 16, comprising:

weighting said image data to give first data;

integrating said first data to give second data;

differentiating said second data to give third data; and dividing said third data by a co-inclination factor to give fourth data.

20. A method as recited in claim 19, comprising:

differentiating said fourth data to give fifth data; and three-dimensionally back-projecting said fifth data.

21. A method as recited in claim 19, comprising:

reconstructing said image using said circle data and said fourth data.

22. A method as recited in claim 19, comprising:

generating said line data using said fourth data.

23. A method as recited in claim 19, comprising:

generating said line data using data at edge planes in said image data.

24. A method as recited in claim 16, wherein approximating line data comprises:

generating line data that will complete a circular data set corresponding to said circle data.

25. A method as recited in claim 16, wherein:

said scanning step produces an incomplete circular data set; and approximating line data comprises generating data to complete said circular data set.

26. A method as recited in claim 16, comprising:

scanning a stationary object along said circular trajectory to obtain said projection data.

27. A method as recited in claim 16, comprising:

generating said approximated line data using edge planes in said circle data.

28. A computed tomography apparatus, comprising:

a cone-beam x-ray source;

an x-ray detector arranged to receive a cone-beam of x-rays emitted from said x-ray source through an object;

a data acquisition device connected to said detector to obtain projection data along a first circular trajectory of said beam around an axis of said object;

a first reconstruction processor connected to said data acquisition device to reconstruct a circle view from the projection data;

a missing data calculator connected to said data acquisition device to calculate data missing from said circle view;

a line data processor connected to said missing data calculator;

a second reconstruction processor connected to said line data processor; and an image addition processor connected to said first and second reconstruction processors.

29. An apparatus as recited in claim 28, wherein:

said data acquisition device obtains projection data along said first circular trajectory of said beam around an axis of a stationary object.

30. An apparatus as recited in claim 28, wherein:

said first reconstruction processor comprises a Feldkamp reconstruction processor.

31. An apparatus as recited in claim 28, wherein said line data processor comprises:

means for weighting data;

means for integrating weighted data;

means for differentiating integrated weighted data; and means for dividing by a co-inclination factor.

32. An apparatus as recited in claim 28, wherein:

said missing data calculator calculates said data using missing from said projection data from edge planes in said projection data.

33. A computed tomography apparatus, comprising:

first means for exposing an object to a cone-shaped beam of x-rays;

second means for detecting said beam of x-rays;

third means for acquiring projection data;

fourth means for reconstructing circular data from said projection data;

fifth means for generating approximated line data from said projection data; and sixth means for reconstructing said image using said circular data and said approximated line data.

34. An apparatus as recited in claim 33, wherein:

said third means comprises means for obtaining projection data along a circular trajectory of said beam around an axis of a stationary object.

35. An apparatus as recited in claim 33, wherein:

said fourth means comprises a Feldkamp reconstruction processor.

36. An apparatus as recited in claim 33, wherein said fifth means comprises:

means for weighting data;

means for integrating weighted data;

means for differentiating integrated weighted data; and means for dividing by a co-inclination factor.

37. An apparatus as recited in claim 33, wherein said fifth means comprises:

means for calculating data missing from said projection data from edge planes in said projection data.

38. A computer program product comprising:

a first code device configured to reconstruct circle data from projection data obtained by scanning an object along a circular trajectory;

a second code device configured to generate approximated line data using said projection data; and a third code device configured to reconstruct an image of said object using said circle data and said approximated line data.

39. A computer product comprising:

a recordable medium containing software programmed to carry out the steps of:

reconstructing circle data from projection data obtained by scanning an object along a circular trajectory;

generating approximated line data using said projection data; and reconstructing an image of said object using said circle data and said approximated line data.

\* \* \* \* \*